(12) United States Patent
Kabany (10) Patent No.: US 11,300,460 B2
(45) Date of Patent: Apr. 12, 2022

(54) MEASURING SYSTEM FOR MEASURING PRESSURE AND/OR HUMIDITY

(71) Applicant: B-Horizon GmbH, Regensburg (DE)

(72) Inventor: Mohammad Kabany, Regensburg (DE)

( * ) Notice: Subject to any disclaimer, the term of this patent is extended or adjusted under 35 U.S.C. 154(b) by 283 days.

(21) Appl. No.: 16/435,719

(22) Filed: Jun. 10, 2019

(65) Prior Publication Data

US 2020/0088589 A1 Mar. 19, 2020

(30) Foreign Application Priority Data

Aug. 1, 2018 (DE) ...................... 10 2018 118 612.6

(51) Int. Cl.
*G01K 13/00* (2021.01)
*G01L 1/14* (2006.01)
(Continued)

(52) U.S. Cl.
CPC .............. *G01K 13/00* (2013.01); *G01L 1/146* (2013.01); *G01N 27/223* (2013.01); *G05B 15/02* (2013.01)

(58) Field of Classification Search
CPC .. G01K 13/00; G01N 33/0075; G01N 27/223; G01N 33/0031; G01B 15/02; G01L 1/146; G01L 1/142
See application file for complete search history.

(56) References Cited

U.S. PATENT DOCUMENTS 5,570,301 A * 10/1996 Barrus ................... A61B 5/103
702/150
6,222,376 B1 * 4/2001 Tenney, III .......... G01N 27/225
324/663

(Continued)

FOREIGN PATENT DOCUMENTS

AT 508976 A1 5/2011
DE 102012208205 A1 11/2013
(Continued)

OTHER PUBLICATIONS

English translation of JP2006078280 description accessed from espacenet.com Aug. 4, 2021.*

(Continued)

*Primary Examiner* — John Fitzgerald
*Assistant Examiner* — Jean F Morello (57) ABSTRACT

The invention relates to a measuring system for measuring pressure and/or humidity, comprising at least one apparatus for measuring pressure and/or humidity, comprising at least one sensor for measuring pressure and/or humidity, wherein the sensor comprises at least one capacitor comprising at least two electrodes that are arranged, in particular, in a horizontal direction along and on an, in particular, flexible support material relative to one another. At least one dielectric layer is arranged between the electrodes. The invention is characterised in that at least one at least partially liquid-permeable and/or liquid-absorbing moisture layer is arranged at least in some places on a side, facing away from a support material, of at least one electrode and/or of the dielectric layer. The at least one electrode and/or the dielectric layer are thus then arranged between the support material and the moisture layer in a transverse direction. In this way, a capacitance is at least partially changed by the liquid at least partially hitting the dielectric layer, wherein a processing unit is designed and provided to measure and/or store measurement values of the sensor. This creates a capacitive moisture sensor. The invention is characterised in that the data measured by the sensor is transmitted by the processing unit to a central CPU, wherein this data is processed by the processing unit.

10 Claims, 5 Drawing Sheets

(51) Int. Cl.
*G01N 27/22* (2006.01)
*G05B 15/02* (2006.01)

(56) References Cited

U.S. PATENT DOCUMENTS

| | | | |
|---|---|---|---|
| 6,742,387 B2 * | 6/2004 | Hamamoto | G01N 19/10 |
| | | | 324/664 |
| 7,213,462 B2 * | 5/2007 | Watanabe | G01N 27/223 |
| | | | 73/714 |
| 9,912,531 B2 | 3/2018 | Neff et al. | |
| 2007/0145985 A1 | 6/2007 | Keep et al. | |
| 2011/0255545 A1 * | 10/2011 | Shin | H04L 12/4641 |
| | | | 370/395.53 |
| 2014/0216153 A1 * | 8/2014 | Pion | G01N 27/225 |
| | | | 73/335.04 |
| 2016/0259473 A1 | 9/2016 | Kim et al. | |
| 2017/0172813 A1 | 6/2017 | Lindström et al. | |

FOREIGN PATENT DOCUMENTS

| | | |
|---|---|---|
| JP | 2006078280 A * | 3/2006 |
| TW | 106203360 U | 3/2017 |
| WO | 2012080689 A2 | 6/2012 |
| WO | 2017210687 A1 | 7/2017 |

OTHER PUBLICATIONS

German Office Action, dated Apr. 25, 2019.
International Search Report, dated Sep. 16, 2019.

* cited by examiner

MEASURING SYSTEM FOR MEASURING PRESSURE AND/OR HUMIDITY

The present invention relates to a measuring system for measuring pressure and/or humidity, as well as to a method for measuring pressure and/or humidity, comprising the preambles of claims 1 and 10, respectively.

The measuring system according to the invention for measuring pressure and/or humidity comprises at least one sensor for measuring pressure and/or humidity, wherein the sensor comprises at least one capacitor comprising at least two electrodes that are arranged, in particular, in a horizontal direction along and on an, in particular, flexible support material relative to one another, wherein at least one dielectric layer is arranged between the electrodes.

The horizontal direction is preferably a main extension direction of the flexible support material.

"Flexible" refers in this context to the support material being bendable and thus resilient at least in some places.

In particular, the support material may be a woven fabric, or another clothing fabric, such as, for example, a polyester.

The dielectric layer thus spaces the two electrodes apart in a horizontal direction and/or transverse direction perpendicular thereto.

According to the invention, at least one at least partially liquid-permeable and/or liquid-absorbing moisture layer is arranged at least in some places on a side, facing away from the support material, of at least one electrode and/or of the dielectric layer, wherein the at least one electrode and/or dielectric layer are thus arranged between the support material and the moisture layer in a transverse direction, such that a capacitance is at least partially changed by the liquid at least partially hitting the dielectric layer, wherein a processing unit is designed and provided to measure and/or store the measurement values of the sensor, so as to create a capacitive moisture sensor.

A capacitive moisture sensor is basically a capacitor having a dielectric that is preferably composed of a hygroscopic polymer layer that, depending on the humidity of the ambient air, takes in (absorbs) or releases (desorbs) moisture until an equilibrium state (where the diffusion gradient=0) is reached. The dielectric constant of the polymer material then changes as a function of moisture content.

The purpose of the processing unit is, inter alia, to determine the relative humidity as accurately as possible, preferably also from a measured ambient temperature and the humidity-dependent capacitance of the sensor.

According to the invention, the data measured by the sensor is transmitted by the processing unit to a central processing unit (CPU), wherein this data is processed by the processing unit. The CPU and the processing unit are preferably different from one another. The CPU and the processing unit are, for example, arranged so as to be spaced apart from one another. In particular, the processing unit and the CPU may not be arranged on a shared support and/or substrate, unless the support is the support material, i.e., for example, a textile.

It may also be envisaged that the apparatus claimed here, and in particular the sensors, are installed on an inner surface of a tyre. It may also be envisaged that the sensors are even inserted into the material of the tyre. It is then conceivable that the sensors have all been inserted into the material and are thus covered by the material of the tyre, and the processing units are arranged on the inner surface of the tyre. As an alternative, however, the processing units may also be inserted into the material of the tyre. The sensors may then capture the internal tyre pressure, the internal tyre temperature, and/or the individual or total lifespan of the tyre.

According to at least one embodiment, the measurement system comprises at least one apparatus for measuring pressure and/or humidity, wherein the apparatus comprises at least one sensor for measuring pressure and/or humidity, wherein the sensor comprises at least one capacitor comprising at least two electrodes that are arranged, in particular, in a horizontal direction along and on an, in particular, flexible support material relative to one another, wherein at least one dielectric layer is arranged between the electrodes.

According to the invention, at least one at least partially liquid-permeable and/or liquid-absorbing layer (=moisture layer) is arranged at least in some places on a side, facing away from the support material, of at least one electrode and/or dielectric layer, wherein the at least one electrode and/or dielectric layer are thus arranged between the support material and the moisture layer in a transverse direction, such that a capacitance is at least partially changed by the liquid at least partially hitting the dielectric layer, wherein a processing unit is designed and provided to measure and/or store these measurement values of the sensor, so as to create a capacitive moisture sensor.

According to the invention, the data measured by the sensor is transmitted by the processing unit to a central processing unit (CPU), wherein this data is processed by the processing unit.

The sensor and/or the processing unit and/or the central CPU may be supplied with electrical energy by means of a battery or a fixed grid power supply.

An alternative or additional possibility is to generate electrical energy for supply to the sensor and/or processing unit by means of so-called "energy harvesting".

Energy harvesting refers to obtaining small quantities of electrical energy from sources such as ambient temperature, vibrations, or air flows for low-power mobile devices. The structures used therefor are also referred to as nanogenerators. Due to wireless technology, energy harvesting avoids the limitations resulting from wired power supplies or batteries.

Possibilities for energy harvesting:
  Piezoelectric crystals generate electrical voltages when subjected to force, for example, through pressure or vibration. These crystals may be arranged at or on the support material.
  Thermoelectric generators and pyroelectric crystals obtain electrical energy from temperature differences. These generators may be arranged at or on the support material.
  Via antennas, the energy of radio waves, a form of electromagnetic radiation, can be captured and used for energy. One example thereof is passive RFIDs. These antennas may be arranged at or on the support material.
  Photovoltaics, electrical energy from ambient light.
  Osmosis.

An energy storage device of the apparatus may be part of a processing unit. For this purpose, one or more of the processing units may comprise such an energy storage device (local energy storage device). For example, only one or some of the processing units has such an energy storage device, such that one of these processing units supplies another processing unit (namely, one that does not have an energy storage device) with electrical energy.

It may also be envisaged that the energy storage unit(s) of the processing unit(s) either fully or partially supply the CPU with electrical energy. For example, thus, the CPU need not be connected to another energy storage device and/or energy supply lines.

At least one of the energy storage devices can be charged via the above-mentioned energy harvesting.

The energy transfer between the sensors and/or the processing units and/or the CPU may take place either wholly or partially wirelessly.

Wireless near-field energy transfer, also called non-radiative coupling, includes, for example, inductive coupling based on the magnetic flux. The term wireless energy transfer is often used as a synonym for inductive energy transfer, because it plays a dominant role in practical applications. Wave phenomena play no role in near-field non-radiative coupling. For example, the wireless energy transfer takes place between the individual elements by means of inductive coupling, resonant inductive coupling, and/or capacitive coupling.

According to at least one embodiment, the measuring system comprises at least two sensors, wherein the processing unit divides the sensors into groups of at least one sensor, on the basis of at least one of the following criteria:
  Place of arrangement of the sensor or sensors on the support material, wherein the support material is divided into surface zones, and within one surface zone only sensors of one group are arranged,
  Surface area of a sensor.

According to at least one embodiment, the measuring system comprises at least two apparatuses for measuring pressure and/or humidity, wherein each processing unit transfers its data received from the sensors to the central CPU. The data link between the processing unit and the central CPU may be wired (by data links), or wireless. For this purpose, at least one processing unit may establish a Bluetooth connection with the central CPU.

According to at least one embodiment, at least one apparatus comprises at least two sensors. In this respect, a sensor group may be formed by just these two sensors. The two sensors may then be controlled in an open and/or closed-loop manner by a shared processing unit.

It can be envisaged that the plurality of processing units constitute a processing network, wherein the acquisition, processing, and/or transfer of the sensor data and/or the processing data of each sensor and/or each processing unit is controlled by at least one control device (master). The control unit may be identical to the CPU described above.

It is, however, also possible for one or more of the processing units controlling the remaining processing units (slaves) and/or the remaining sensors (slaves) to represent the master.

For example, one of the processing units and/or the CPU may, after startup of the apparatus (for example, after the apparatus has been switched on), select sensors that are started up for a predeterminable period of use. Alternatively, all or some sensors may be started up, though it is then conceivable that a processing unit and/or the CPU only transfers data of a predetermined number of sensors (i.e. fewer than all of the sensors) to the CPU (filtering), in particular in order to conserve energy.

This master processing unit may preferably communicate as a single unit with the CPU.

Also alternatively or additionally, it is conceivable that one or all of the processing units and/or a sensor (slave or master) communicates directly with the CPU.

According to at least one embodiment, the processing network can be divided by means of at least one VLAN switch into at least two network segments (VLANs) that are separated only logically from one another, and wherein each of the acquisition elements can be controlled in accordance with the control by a VLAN switch and/or the control device and thus by each of the network segments.

If, for example, a very large surface (for example, a textile) is equipped with a plurality of claimed sensors and processing units, it is especially easy to then categorise individual processing units and/or sensors (according to different priorities, and the like). Thus, in one embodiment, a "virtual", i.e. VLAN, division is chosen instead of a physical network division. This namely ensures the ability to react to changes in the categorisation of the processing units and/or sensors especially quickly and without costly alteration work.

According to at least one embodiment, the measuring system comprises at least one processing network, wherein the processing network can be divided by means of at least one VLAN switch thereof into at least two network segments (VLANs) that are only logically separated from one another, and wherein each of the processing units and/or each of the sensors can be actuated in accordance with the actuation by the VLAN switch through each of the network segments.

For this purpose, the VLAN switch may be installed in at least one of the processing units and/or sensors, or in a separate component.

According to at least one embodiment, the VLAN switch carries out prioritisation of the individual network segments, in particular with regard to the data exchange thereof.

According to at least one embodiment, at least one VLAN ID is assigned to each processing unit and/or each network segment, wherein at least one sensor or another processing unit can be actuated via each of the VLAN IDs. Individual sensors and/or individual processing units may form a private subnetwork.

In order to communicate over network boundaries, static project-dynamic routers are used in the prior art. This model of separation is clear and understandable, and has been applied for years. However, this mode is disadvantageous in that broadcast requests in the subnetwork are visible to all participants, and would have to be viewed from the endpoints. In other words, it has thus far only been possible to actuate different terminals via corresponding switches that are associated with each subnetwork, and are separate and physically isolated from one another. Such a structure is, however, especially costly and bulky in design.

As mentioned above, in particular the design of each subnetwork with a separate switch and separate physical data lines is thus forgone, such that a single physical structure can be applied for the entire network, wherein this physical structure, i.e. the network architecture, is only separated on the basis of a logical, in particular also mathematical distinction (i.e. virtually).

The abbreviation "VLAN switch" refers here to a network switch that is designed and provided to operate a network in the form of a virtual local area network (VLAN).

In this respect, the now-claimed network segments, which may each be configured in the form of a VLAN network, thus make it possible to divide the separation of the network into a plurality of logical segments, i.e. the network segments.

Unlike with physical separation by assignment to a switch port, the devices are separated logically by a VLAN ID in the event of separation by VLANs. Then, the data stream of each station is provided with an identifier (the VLAN "tag"). This identifier determines the association of a data packet with a specific VLAN. All devices that have the same VLAN ID are now located in a logical network.

In particular, namely the logical separation of the individual networks may limit broadcasting. Broadcasts are, namely, only distributed to members of the same VLAN and not to all of the control elements attached to the switch.

This contributes, in this respect, not only to higher power, but also to more security, as the data traffic will be restricted to fewer recipients. In addition, users or the control elements generally have, in a VLAN, no ability to break out of the assigned VLAN. Access (or attack) on another computer that does not belong to the private VLAN can therefore already be prevented by the network switch. If a VLAN is needed for comprehensive communication, routes may be set up explicitly for this purpose.

In particular, it is noted that the VLAN technology described here may be one that is adapted to the industry standard IEEE 802.1Q and/or is compatible therewith.

The IEEE 802.1Q standard is prioritisation and VLAN technology that has been standardised by the IEEE and implements packet-based tagged VLANs, in contrast with older, only port-based VLANs. The expression "tagged" is derived from the expression "material tags".

Tagged VLANs are therefore networks that use network packets bearing a special VLAN marker.

In particular, namely, the 802.1Q standard defines data fields for V-LAN tagging that can be introduced in the data region of an Ethernet packet.

In this respect, the present network may be configured in the form of an Ethernet communication system.

An advantage thereof is that even already-existing, older switches are generally able to transfer such packets. The inserted tag is generally composed of a plurality of fields, for example four fields having a total length of 32 bits.

Two bytes are used for the protocol ID, 3 bits for the priority field, 1 bit for the indicator of the canonical format, and 12 bits for the VLAN ID.

First, a unique number is therefore assigned to each VLAN in order to uniquely identify a VLAN. This number is called a VLAN-ID. A detection module that is equipped with VLAN ID=1 can communicate with each other device in the same VLAN, but not with a device in a different VLAN, such as with, for example, ID=2, 3, and so forth.

In order to distinguish between the VLANs, an Ethernet frame is extended by 4 bytes in accordance with the IEEE 802.1Q standard. 12 bits thereof are provided to accommodate the VLAN ID, and so theoretically 4096−2=4094 VLANs are possible (without use of the canonical format).

It would be conceivable to configure the individual logical network connections in accordance with an OPC standard, i.e. for example, in the form of OPC UA connections. In particular, namely, it would be conceivable to make a plurality of OPC UA endpoints available per network segment, via the control device, with a different IP address, VLAN ID, and prioritisation in accordance with the aforementioned standard IEEE 802.1Q.

If, now, a network segment that has received a uniquely, preferably unambiguously, assigned specific VLAN ID has a higher priority than a network segment, differing therefrom only in terms of logic, of a correspondingly different VLAN ID, then the control device and/or the VLAN switch may be provided to first prefer the data exchange of the higher-priority network segment, in order to enable processing of the lower-priority network segment only after the tasks associated with this higher-priority network segment have been resolved.

In other words, in general: assignment and configuration of the OPC UA endpoints to a specific network segment according to the VLAN ID, as well as assignment of a priority according to the priority of the corresponding VLAN.

According to at least one embodiment, at least one VLAN ID is assigned to each sensor and/or each processing unit, and at least one, for example exactly one, unique, preferably unambiguous VLAN ID is assigned in turn to each network segment, wherein at least one control element can be actuated via each one of the VLAN-IDs. According to at least one embodiment, at least one apparatus comprises at least one temperature sensor, wherein the temperature sensor measures an ambient temperature and/or a temperature of a sensor, and transfers same to the processing unit of an apparatus and/or to the central CPU.

According to at least one embodiment, the central CPU determines a degree of loading (CPU load and/or memory consumption) of at least one processing unit, wherein if a limit temperature of the processing unit and/or at least of the sensor associated with this processing unit is exceeded, said unit or sensor is at least partially throttled in terms of its power or is completely shut down.

According to at least one embodiment, the sensor is additionally a capacitive pressure sensor, wherein the processing unit is additionally designed and provided to measure and/or store a change in capacitance of the capacitor caused by external pressure.

Basically, a capacitive sensor is thus a sensor that works on the basis of the change in the electrical capacitance of an individual capacitor or of a capacitor system. The capacitance may be affected in different manners by the variable to be acquired, which is determined primarily by the intended use.

A capacitive sensor is based, inter alia, on two electrodes, one of which may be the surface to be measured, forming the "plates" of an electrical capacitor, the capacitance of which or a change in the capacitance of which is measured, and may be affected as follows:

One plate is displaced and/or deformed by the effect to be measured, whereby the spacing of the plates and thus the measurable electrical capacitance are altered.

The plates are rigid, and the capacitance thereof changes when an electrically conductive material or a dielectric is brought into the immediate vicinity.

The effective plate area is altered by displacement of the plates relative to one another, as with a variable capacitor.

In order to be better able to detect even small changes, the actual measuring electrode is often surrounded by a shield electrode, which shields the non-homogeneous edge region of the electrical field from the measuring electrode, thereby producing, between measuring electrodes of a typically grounded counter-electrode, a substantially parallel electrical field with the known characteristics of an ideal plate capacitor.

A capacitive pressure sensor is, in particular, one with which the change in capacitance as a result of flexing of a membrane and the resulting change in the plate spacing is evaluated as a sensor effect. For example, the membrane may be the above-mentioned dielectric, or the individual capacitor electrodes, which may be configured, in particular, in the form of a plate. In other words, in such an embodiment, a capacitive moisture sensor is combined in a novel manner with a capacitive pressure sensor, but without these components forming separated elements or two distinct sensors, but rather the present embodiment involves a "twoin-one" concept, where the same sensor functions both as a moisture sensor and as a pressure sensor.

According to at least one embodiment, the support material is a woven fabric, in particular into which conductor paths are woven for electrical contact between the sensor and the processing unit.

A woven fabric within the meaning of the invention is therefore a fabric that has been woven manually or by machine on the basis of individual threads.

The electrical conductor paths may therefore be additionally integrated in a fabric, in addition to the usual fibres and fabric strands, or may replace individual fabric strands constituting the fabric mesh.

Depending on the distance and the properties of the individual threads (high-twist, bulked, etc.), a rather loose fabric may be produced, such as a dressing fabric, or a dense fabric such as brocade material. With longitudinal resilience, fabrics are used by rubber threads (more bands used) used as warp yarns, or crimped and bulked yarns. They are tensioned, processed, and contracted in the resting state. Bulked yarn is composed of textured, i.e. crimped synthetic fibres. The crimping alters the properties of the synthetic fibres. The yarn spun thereon is very resilient and voluminous, and has favourable thermal insulation.

For example, the support material may be part of an upholstery material of a seat, in particular, a vehicle seat or an office chair. In this respect, the sensor, but preferably the entire apparatus, may be installed on the upholstery material of such a seat or integrated therein.

For example, the processing unit is designed and provided to acquire the individual moisture and pressure values, and to determine, from a combination of the individual moisture and pressure values, at least one particular characteristic value from which it is possible to derive which individual (by weight and/or size) has just occupied the vehicle seat.

For example, from the pressure measurement by the processing unit, it is possible to derive and establish a weight of the respective person. The particular humidity that the respective person gives off to the sensor may also be measured, wherein the respective characteristic value is, for example, the product of the relative humidity value times the load weight determined by the processing unit.

If such a characteristic value exceeds a corresponding limit value, then the processing unit may issue a warning, in particular by means of a connection to the electronics of the vehicle. This warning may be to the effect that the seat is overloaded or that the driver is sweating too intensely. This warning, may also, however, be replaced by a corresponding display as to what occupancy type is using the seat. An occupancy type may entail a weight classification for a particular user, or may entail whether the user is an animal, a human, or an object. Preferably, therefore, the processing unit can be integrated into display electronics of the vehicle, or at least can be connected thereto.

For this purpose, it would be conceivable for the processing unit to connect, for example, by means of Bluetooth or another wireless connection to a receiving unit of the vehicle, and for the respective characteristic value or limit value and/or the respective warning and/or the respective identifier of the user to be played back on a display of the vehicle.

Alternatively or additionally thereto, it would also be conceivable for it to be possible to externally retrieve and/or externally display these individual values and/or identifiers. For example, the car may be monitored for occupancy by an external controller.

For example, the processing unit may, by means of a data link, be connected to a triggering unit of an airbag, so that the processing unit can also control the triggering unit in an open and/or closed-loop manner, in particular in relation to a triggering time point of the airbag. Additionally or alternatively thereto, it is also possible for the processing unit to supply a controller unit of the airbag with data, for example with respect to an occupancy type, position, and/or weight of a user of the vehicle seat.

This data may cause the triggering time point and the triggering sequence of the airbag to be adapted to the user, so as to prevent personal injury to the user.

According to at least one embodiment, at least one electrode and/or dielectric layer is printed or applied by means of a thin-layer method onto the support material or onto an, in particular, water-impermeable layer arranged on the support material.

This means that at least one element, preferably both the electrode and the dielectric layer, are printed by means of a printing method onto the support material or a preferably non-electroconductive, further preferably water-impermeable layer that has been applied between the sensor and the support material.

The printing method may entail, for example, an inkjet method.

For example, the processing unit is applied to the support material in the same manner as the sensor. For this purpose, it would be conceivable, for example, to also print the processing unit, or at least one, in particular conductive, layer of the processing unit onto the support material. The data communication between the processing unit and the sensor may then occur via the above-mentioned conductor paths. These conductor paths may be woven at least partially, but preferably entirely, into the fabric, or may even themselves constitute individual fibres of the fabric.

For example, at least one electrode is configured so as to be flat. This means that a thickness of the electrodes is negligible in comparison to the surface area thereof. Such an electrode may therefore be produced, in particular, by means of a printing method.

As an alternative thereto, a thickness of at least one electrode may be at most 5 mm. For this purpose, the printing method may be applied several times, so that at least two, but preferably even more, individual pressure layers are stacked one over the other.

The electrodes may also be arranged on the support material by means of a 3D printing method.

1. The Fused Deposition Modelling (FDM) Method

Alternative names: fused filament fabrication (FFF), fused layer modelling (FLM)

The method refers to layered deposition (extrusion) of a material through a hot nozzle. The consumable material is in the form of a long wire (so-called filament) on a roll and is pushed by the conveyor unit into a print head, melted therein, and deposited onto a print bed. In the process, the print head and/or print bed are movable in three directions. Layers of plastics can thus be deposited in stages on top of one another.

2. The Selective Laser Sintering (SLS) Method

Unlike the sintering method, in which materials in powder form are combined with one another under the effect of heat, this occurs selectively in the SLS method using a laser (alternatively also an electron beam or infrared beam). Therefore, only a certain quantity of the powder is molten together.

For this purpose, a thin layer of powder is constantly output by the layering unit onto the print bed. The laser (or other energy source) is now precisely aligned with individual points on the powder layer in order to form the first layer of print data. In the process, the powder is melted or fused and then solidifies again as a result of slight cooling. The powder that has not been fused remains lying around the sintered regions and serves as a support material. After one layer has solidified, the print bed is lowered by a fraction of a millimetre. The layering unit now travels across the print bed and outputs the next layer of powder. Subsequently, the second layer of print data is sintered by the laser (or another energy source). A three-dimensional object thus emerges gradually.

3. Three-Dimensional Printing (3DP)

The 3DP method functions very similarly to selective laser sintering, but instead of a directed energy source, a print head travels over the powder. This releases tiny droplets of binding agent onto the underlying powder layers, which are thus connected to one another. This method is otherwise identical to the SLS method.

4. Stereolithography (SLA)

Instead of a plastics wire or print material in powder form, liquid resins, so-called photopolymers, are used in the stereolithography method. They are hardened in layers by UV radiation and thus produce three-dimensional objects. For this purpose, the platform is lowered gradually in the resin vat. There are also variants (so-called polyjet methods) without an entire vat with liquid resin. For this purpose, an epoxy resin is applied out of a nozzle droplet by droplet and immediately hardened by a UV laser.

5. Laminated Object Manufacturing (LOM)

Alternative name: layer laminated manufacturing (LLM)

The method is based on neither chemical reactions nor a thermal process. In the process, a film or plate (for example, paper) is cut along the contour using a cutting tool (for example, a knife or carbon dioxide laser) and bonded in layers on top of one another. A layered object of bonded films laid on top of one another is thus produced by lowering the platform.

One or more water-impermeable layers and/or even the moisture layer may be applied in the same manner and/or thickness as the electrode.

According to at least one embodiment, the moisture layer completely covers the capacitor.

This may mean that the moisture layer delimits and closes off the sensor from the outside, i.e. in the transverse direction, such that the sensor is arranged between the moisture layer and the support material.

According to at least one embodiment, the sensor comprises at least one other capacitor, which is arranged below or above the capacitor in the transverse direction and is arranged on or under another water-impermeable layer so as to be spaced apart from the capacitor by this other water-impermeable layer, thus creating a capacitor stack.

The other capacitor may be constructed in the same manner as the capacitor, and also arranged in the same manner as the capacitor on the other water-impermeable layer.

Such a capacitor stack makes it very easy to refine the sensors, namely in that it is conceivable that with two sensors constituting the capacitor stack, both sensors would perform the same tasks, but the individual sensors would determine respective measurement values that could then be used to find an average value. For example, the (relative) humidity of the environment is measured by each of the two sensors, wherein the mean humidity value is determined from these two measurement values. The same may occur accordingly with the pressure measurement, thus enabling an especially exact accuracy of the overall measurement, in particular of a combination of the measurements of (relative) humidity and the respective pressure.

According to at least one embodiment, the water-impermeable layer and/or the other water-impermeable layer at least partially constitutes the dielectric layer.

This may mean that instead of the separate positioning of a dielectric layer beside the water-impermeable and/or beside the other water-impermeable layer, this dielectric layer may itself be formed by the water-impermeable layer and/or the other water-impermeable layer.

Such a production of the dielectric layer by the water-impermeable layer(s) therefore forms an especially easy and low-cost method of production for a low-cost apparatus.

Apart from that, it may basically be provided that the electrodes, the dielectric layer, and the water-impermeable layer(s) are arranged in such a manner in relation to one another that an electrical short-circuit can at least be prevented.

According to at least one embodiment, a maximum thickness of the moisture layer amounts to at least 30% and at most 80% of the maximum thickness of the water-impermeable layer and/or the maximum thickness of the other water-impermeable layer.

This not only ensures a sensor that is built to be especially flat, but also guarantees an especially quick response time to changes in humidity. Therefore, the humidity acting on the moisture layer from the outside need not pass through large distances to reach the dielectric.

The present invention also relates to a method for measuring pressure and/or humidity, wherein it should be noted in particular that all of the features disclosed for the apparatus described above are also disclosed for the method described here, and vice versa.

According to at least one embodiment, the method for measuring pressure and/or humidity initially comprises a first step by means of which at least one measuring system, in particular according to at least one of the preceding claims, is provided, wherein the measuring system provides at least one sensor for measuring pressure and/or humidity, wherein the sensor comprises at least one capacitor comprising at least two electrodes that are arranged, in particular, in a horizontal direction along and on an, in particular, flexible support material relative to one another, wherein at least one dielectric layer is arranged between the electrodes.

According to the invention, at least one at least partially liquid-permeable and/or liquid-absorbing moisture layer is arranged at least in some places on a side, facing away from the support material, of at least one electrode and/or of the dielectric layer, wherein the at least one electrode and/or the dielectric layer are thus arranged between the support material and the moisture layer in a transverse direction, such that a capacitance is at least partially changed by the liquid at least partially hitting the dielectric layer, wherein a processing unit measures and/or stores this change, so as to create a capacitive moisture sensor.

The method described above then has the same advantages and advantageous configurations as the apparatus described above.

The invention described here shall be described in greater detail below with reference to two embodiments and the corresponding drawings.

Like components or similarly-behaving components are provided with like reference signs.

Figure 1A:
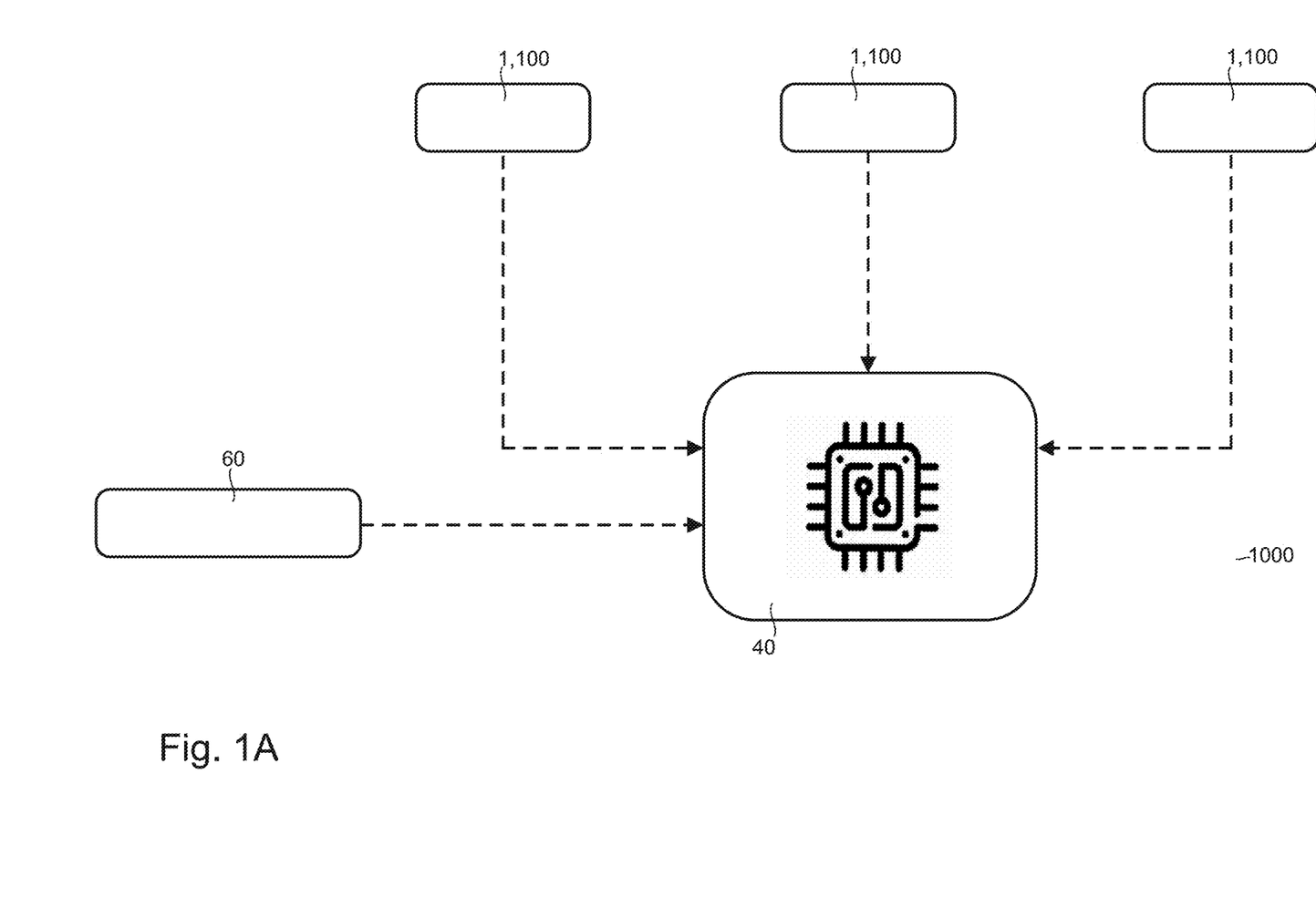
FIG. 1A to 1C show an embodiment of a measuring system described here according to the invention.

FIG. 1A shows a portion of a schematic construction of a measuring system 1000 described here according to the invention. The drawing shows a processing unit 5, which is in data communication with a plurality of sensors 1. The processing unit 5 forms an apparatus 100 together with the sensors 1. The humidity and/or pressure values measured by the individual sensors 1 are transmitted to a central CPU 40 in order to be stored and/or further processed there. Also present is a temperature sensor 60 that measures an ambient temperature and/or a temperature of the sensor 1 and forwards same to the processing unit 4 of the apparatus 100 and/or to the central CPU 40.

Figure 1B:
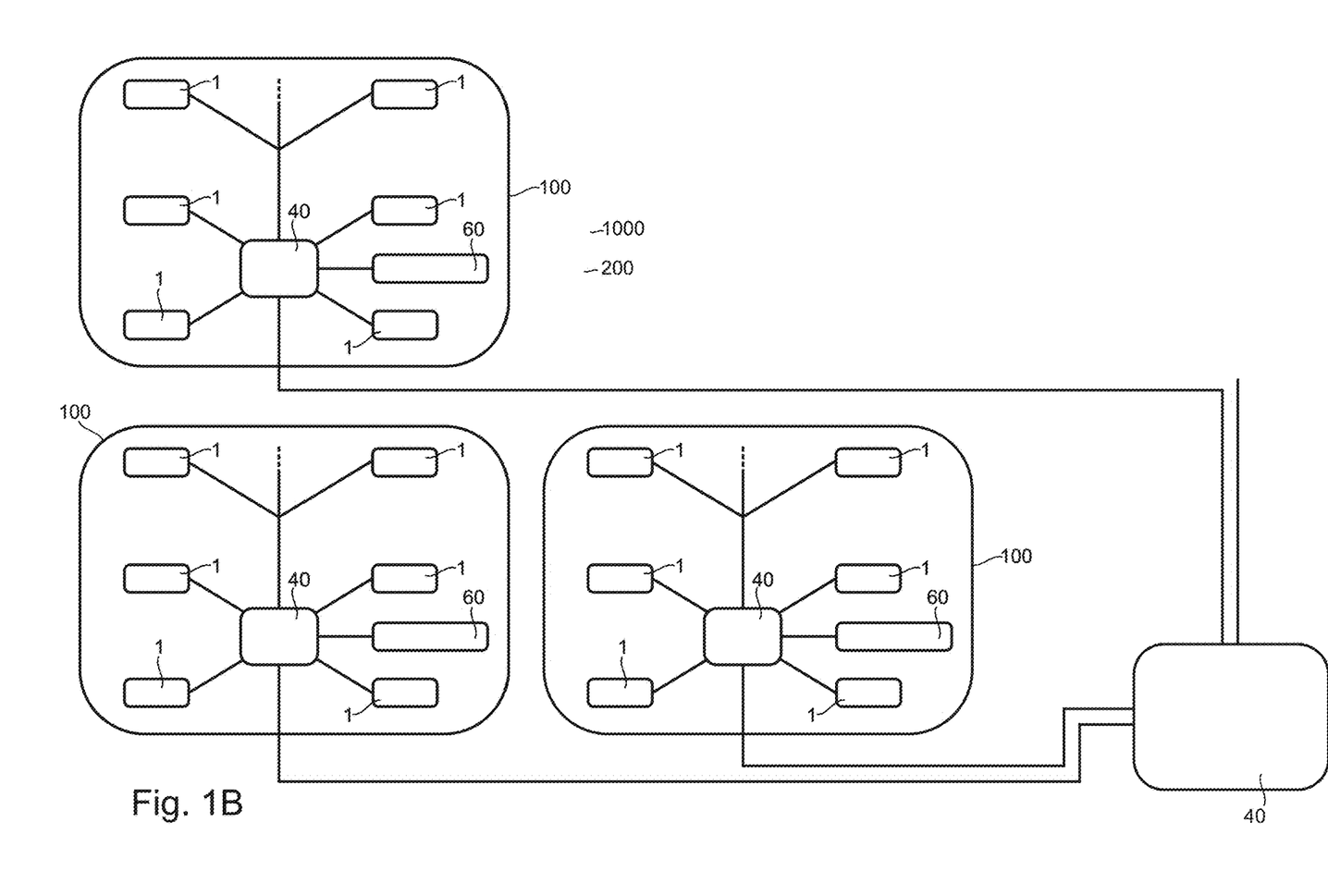

FIG. 1B schematically illustrates the entire measuring system 1000, comprising a plurality of sensor groups that are formed by the individual apparatuses 100 for measuring pressure and/or humidity and each show a processing unit 5. Each processing unit 5 is therefore associated with a plurality of sensors 1.

Figure 1C:
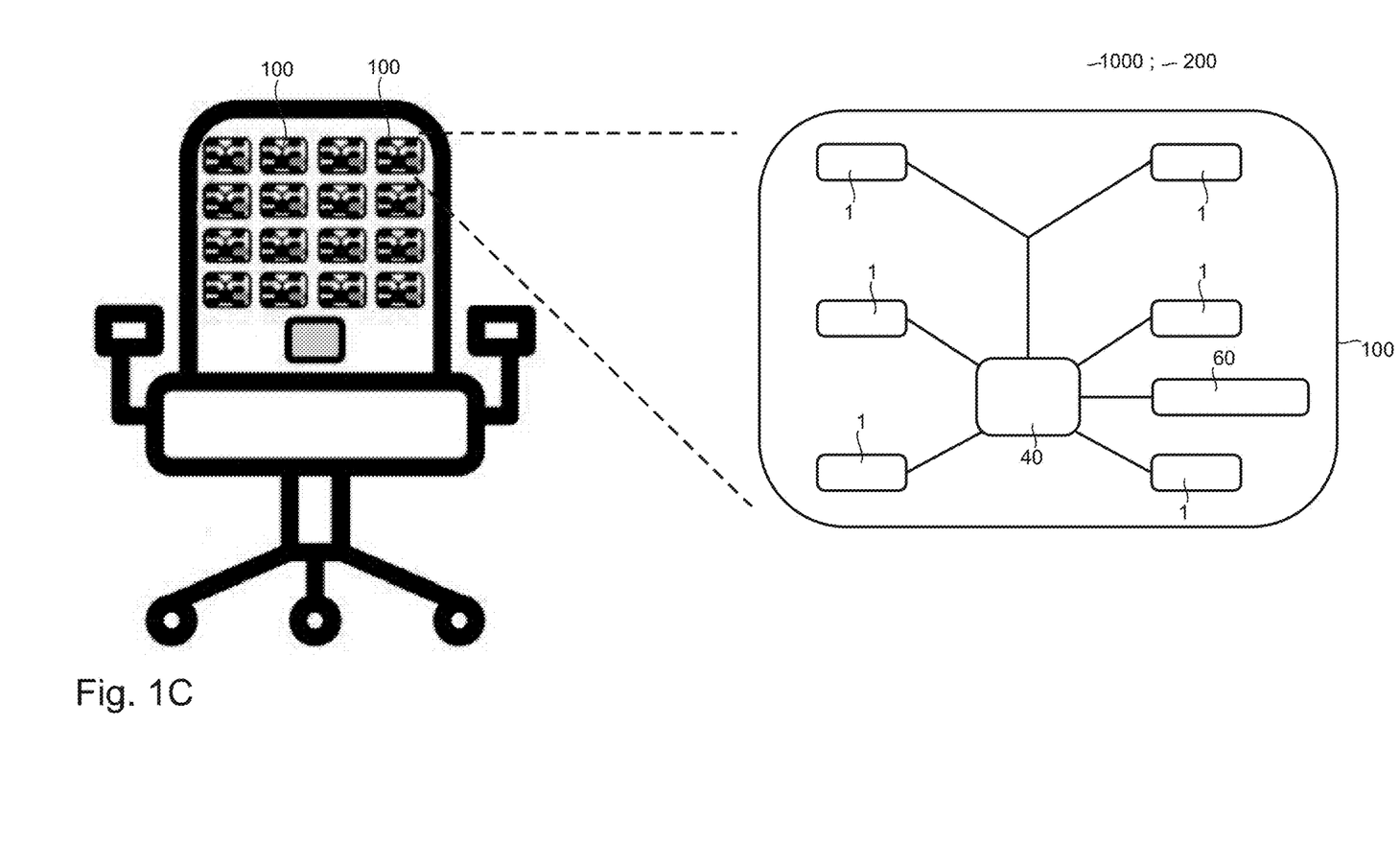

FIG. 1C schematically illustrates an installation and integration of the measuring system 1000 into a chair, in particular an office chair.

Figure 2:
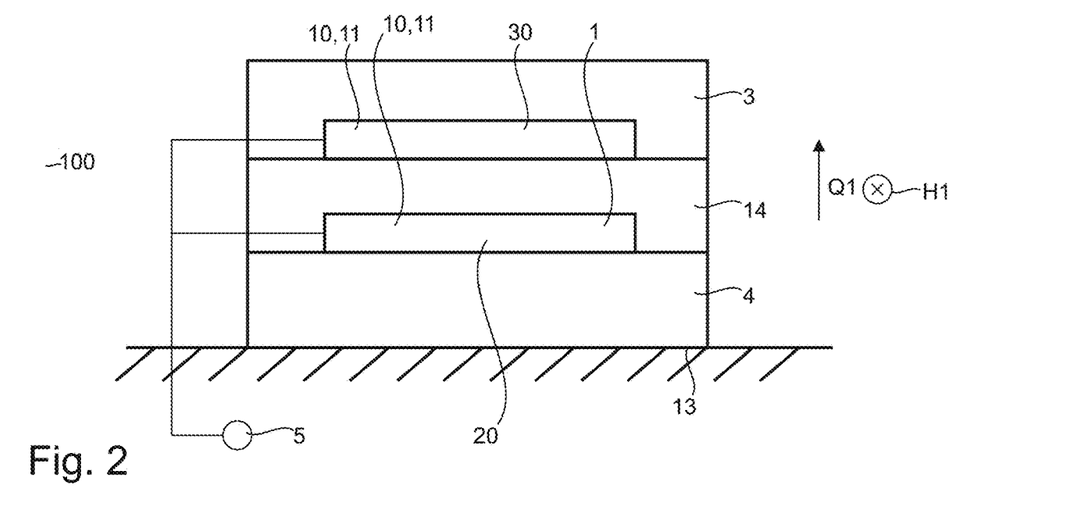
FIG. 2 shows a first embodiment of an apparatus according to the invention for measuring pressure and/or humidity.

As can be seen in FIG. 2, an apparatus 100 for measuring pressure and/or humidity is illustrated therein.

A sensor 1 is depicted by way of example therein, wherein the sensor 1 shows a capacitor stack comprising a capacitor 20, as well as a capacitor 30, wherein the individual electrodes 10, 11 of the capacitors 20, 30 are arranged over one another in the horizontal direction H1, wherein it goes without saying that, as an alternative thereto, however, an assembly of the individual electrodes 10, 11 of an individual capacitor 20, 30 may run or be arranged in the transverse direction Q1, which runs perpendicularly to the horizontal direction H1, and thus also perpendicularly to the main extension direction of the sensor 1 illustrated therein.

The individual electrodes 10, 11 are arranged on a support material 13. The support material 13 may be, in particular, a woven fabric, in particular a flexible woven fabric.

A water-impermeable layer 4 is arranged on the support material 13, wherein the two electrodes 10, 11 of the capacitor 20 are printed in the horizontal direction H1 on this water-impermeable layer 4.

The electrodes 10, 11 of the capacitor 20 are completely surrounded by another water-impermeable layer 14. The other capacitor 30, comprising corresponding electrodes 10, 11, is printed on this water-impermeable layer 14 in the same form and manner. In addition, in the present embodiment, exposed outer surfaces of the individual electrodes 10, 11 of the other capacitor 30 are preferably completely surrounded by a water-permeable and/or water-absorbing moisture layer 3.

Via this moisture layer 3, water can hit a dielectric layer 4, which in the present case is arranged between the respective electrodes 10, 11 of a capacitor 20, 30 in the horizontal direction H1.

Figure 3:
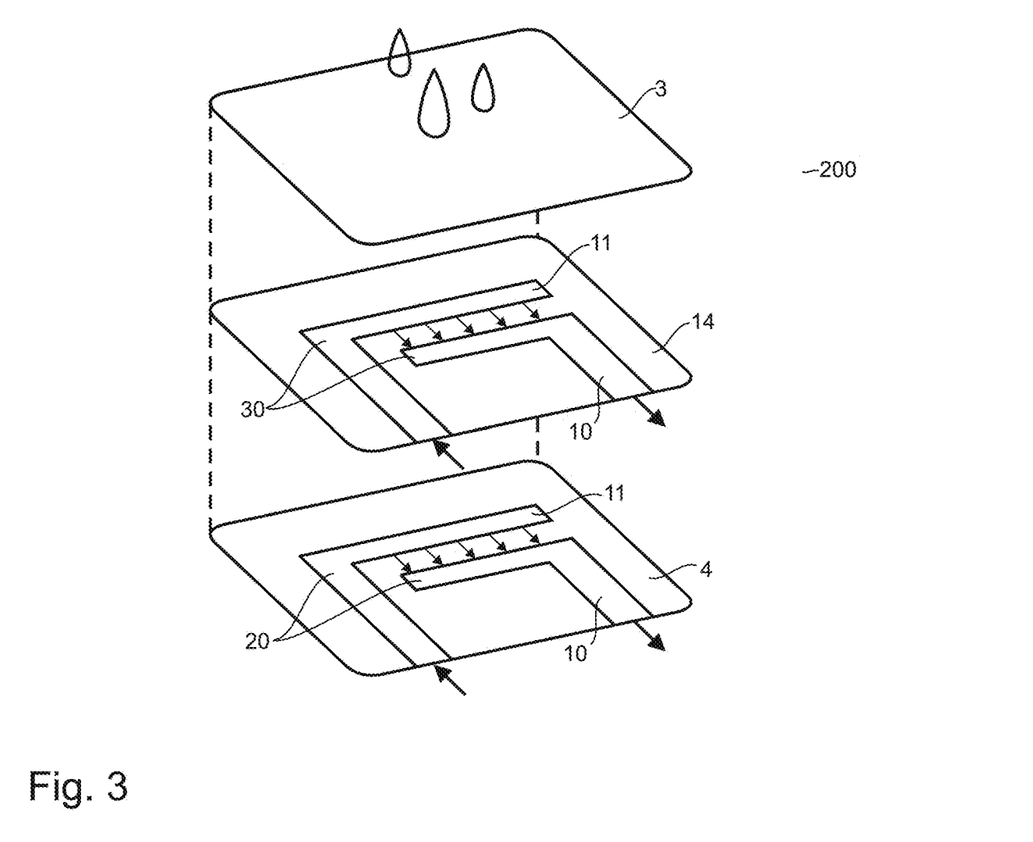
FIG. 3 is a schematic perspective view of an exploded drawing, depicted in relation to the order of layers.

In the present embodiment of FIGS. 2 and 3, the water-impermeable layer 4 itself constitutes a dielectric layer 4 of the capacitor 20. The same is true for the other water-impermeable layer 14 in relation to the other capacitor 30.

Impact and penetration of the humidity through the moisture layer 3 alter the dielectric properties, in particular, of the dielectric layer 4 of the other capacitor 30.

Also visible is a processing unit 5 that has a data connection with the two capacitors 20, 30, wherein this processing unit 5 is designed and provided to measure a change in the relative humidity of the environment and/or of the moisture layer 3.

The "stackwise" arrangement depicted in FIG. 3 and the fact that the other water-impermeable layer 14 prevents the capacitor 20 from coming into contact with humidity may therefore provide that only the other capacitor 30 and the dielectric layer 4 thereof are exposed to the humidity. For this purpose, the processing unit 5 may then compare a change in the capacitance of the other capacitor 30 with the stable capacitance of the capacitor 20, such that, for this purpose, an especially simple comparison may be produced in the change in the relative humidity and/also in the respective load pressure.

The arrow depicted in FIG. 2 also illustrates a direction of pressure in which the sensor 1 is subjected to pressure. Both can preferably be measured, evaluated, and stored by the sensor 1 and, in particular, by the apparatus 100. This is achieved in particular by the processing unit 5, which is presented as being essential in the invention and can also additionally measure and evaluate corresponding pressure values and, in this respect, related changes in the capacitance of the individual sensors 1, such that the processing unit 5 is additionally designed and provided to measure and/or store a change, caused by external pressure, in the capacitance of the capacitor 20 and, in particular, also of the other capacitor 30.

The moisture layer 3 may be configured so as to be flexible or non-flexible. It is also possible for the moisture layer 3 to be configured as a woven fabric. In particular, it may be a woven fabric that was mentioned by way of example in the introductory part of the present application. It is, however, also possible for the moisture layer 3 to be a substrate that is applied, for example adhered, to the other capacitor 30, for example in the form of an epitaxy or bonding process.

The water-impermeable layer 14 and/or the water-impermeable 15 may also be flexible and non-flexible, in particular may also be formed as a woven fabric or a substrate in the same manner as the moisture layer 3.

It may also be advantageously envisaged for the electrodes 10, 11 of the two capacitors 20, 30 to be printed onto the water-impermeable layer 14 and the other water-impermeable layer 15 in the form of a printing process, for example an ink jet printing process.

FIG. 3 illustrates an exploded view, wherein, in particular, the respective arrangement of the electrodes 10, 11 of the capacitors 20, 30 emerges from FIG. 3. Also visible, in turn, is the direction of force, represented by the direction of the arrow, on the sensor 1, as well as the humidity acting through the individual, schematically depicted drops. In particular, it is again evident that the humidity penetrates, in particular between the electrodes 10, 11, and has a, for example, significant effect on the electrical property at the particular water-permeable layer 14, such that the capacitance of at least the other capacitor 30 changes, as explained in FIG. 1.

Figure 4:
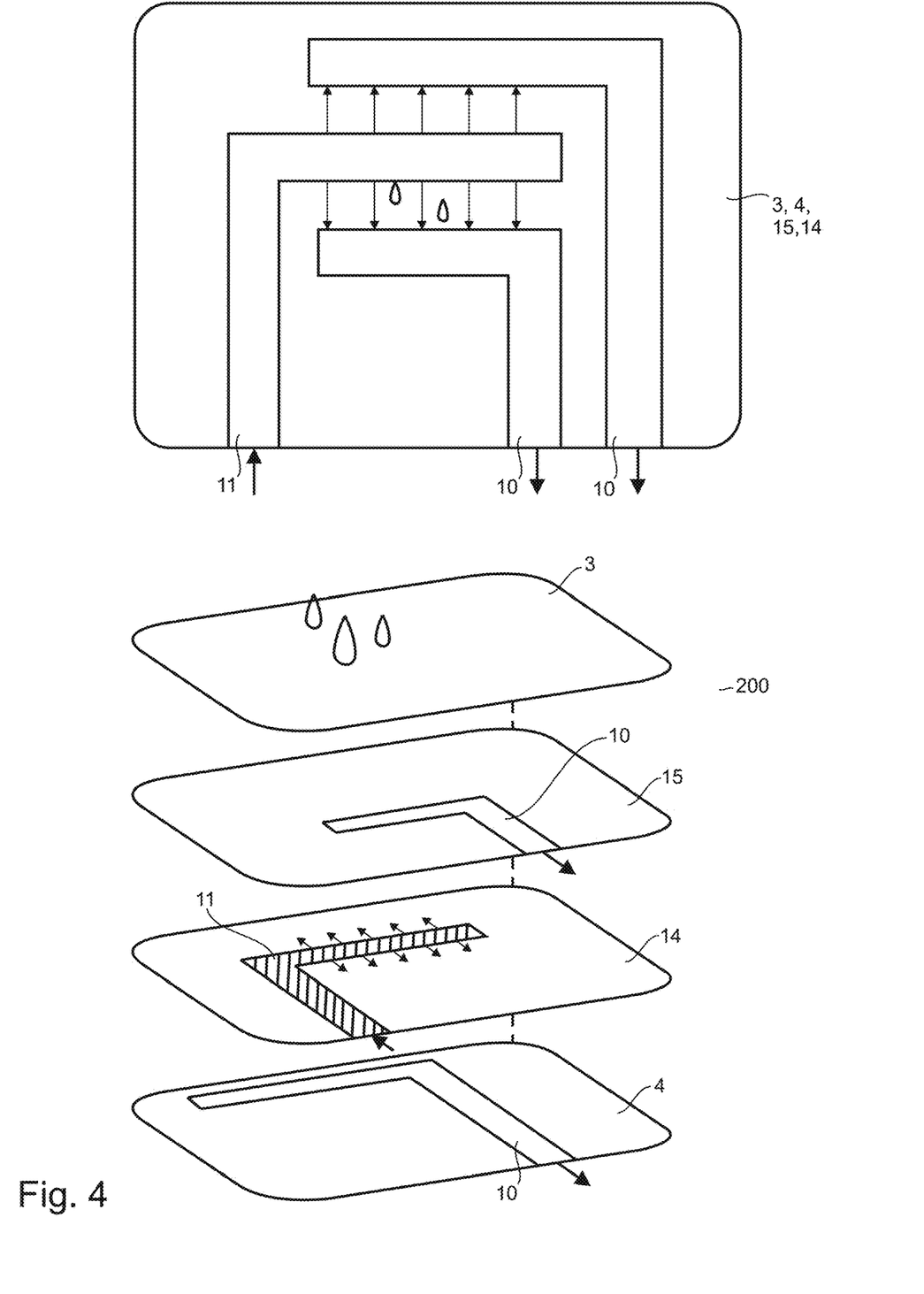
FIG. 4 shows another embodiment of an apparatus described here.

In another embodiment of the invention described here, FIG. 4 illustrates that the sensor 1 may be composed of two electrodes 10 and one electrode 11. The electrodes 10 have one polarity (preferably the same polarity), whereas the electrode 11 has a different polarity therefrom, wherein, however, the exploded view of the left part of FIG. 3 in the lower part of FIG. 3 illustrates and shows that three water-impermeable layers 4, 14, 15 are used. The electrodes 10 may also have different polarities and/or electrical potentials. The electrodes 10 may also be electrically connected to one another.

For example, the electrodes 10, 11 may also each have and/or generate a distinct polarity and/or a distinct electrical potential. The same may also apply to the ones in the following drawings in relation to the electrodes.

For example, the lowermost water-impermeable layer is in turn the water-impermeable layer 4, and the subsequent water-impermeable layer 14 and the water-impermeable layer 15 arranged thereon in the transverse direction Q1 are another water-impermeable layer, wherein in each case an electrode is applied, in particular printed, onto a separate water-impermeable layer.

This stacking of the individual water-impermeable layers 4, 14, and 15, by merging these layers, therefore produces the capacitor 20 illustrated in the left part of FIG. 4, wherein in this case, in the transverse direction Q1, the electrodes 10 are each arranged on different planes, as can be seen in the corresponding partial view.

As an alternative hereto, the electrode 11 may also be applied with at least one of the electrodes 10 in a shared plane, i.e., on or in a shared water-impermeable layer 4, 14, 15, such that, for example, only the second one of the electrodes 10 still needs to be stacked onto a separate water-impermeable layer 4, 14, 15.

In principle, therefore, the individual electrodes 10, 11 may be arranged in different planes relative to one another in the Q1 direction, for example a pairwise association of precisely one water-impermeable layer 4, 14, 15 with precisely one electrode 10, 11.

The invention is not limited by the description with reference to the embodiment. Rather the invention encompasses every novel feature, as well as every combination of features, including, in particular, every combination of features in the claims, even if such feature or combination is not itself explicitly set forth in the claims or in the embodiments.

LIST OF REFERENCE SIGNS

1 Sensor
3 Moisture layer
4 Dielectric layer/water-impermeable layer
5 Processing unit
10 Electrode
11 Electrode
12 Electrode
13 Support material
14 Water-impermeable layer
15 Water-impermeable layer
20 Capacitor
30 Capacitor
40 CPU
60 Temperature sensor
100 Apparatus
200 Method
1000 Measuring system
H1 Horizontal direction
Q1 Transverse direction

The invention claimed is:

1. A measurement system (1000) for measuring pressure and/or humidity comprising at least one apparatus (100) for measuring pressure and/or humidity, comprising at least one sensor (1) for measuring pressure and/or humidity, wherein the sensor (1) includes,
at least a first capacitor (20) comprising at least two electrodes (10, 11) that are arranged, in a horizontal direction (H1) along and on a flexible support material (13) relative to one another, wherein at least one dielectric layer (4) is arranged between the electrodes (10, 11), wherein
at least one at least partially liquid-permeable and/or liquid-absorbing moisture layer (3) is arranged at least in some places on a side, facing away from the support material (13), of at least one electrode (10, 11) and/or of the dielectric layer (2), wherein the at least one electrode (10, 11) and/or the dielectric layer (4) are thus arranged between the support material (13) and the moisture layer (3) in a transverse direction (01), such that a capacitance is at least partially changed by the liquid at least partially hitting the dielectric layer (4), wherein a processing unit (5) is designed and provided to measure and/or store measurement values of the sensor (1), so as to create a capacitive moisture sensor, and wherein
the sensor (1) has at least a second capacitor (30) which is arranged in the transverse direction (Q1) above or below the first capacitor (20) and is arranged spaced apart from the first capacitor (20) by a further water-impermeable layer (14) on or below this further water-impermeable layer (4), so that a capacitor stack is formed, and further wherein
both capacitors (20, 30) are constructed in the same way, and further wherein the two sensors forming the capacitor stack perform the same tasks, and
the measuring system (1000) comprises at least two sensors (1), wherein by the processing unit (5) the sensors (1) are divided into groups of at least one sensor (1) based on at least one of the following criteria:
arrangement location of the sensor (1) or sensors (1) on the carrier material (13), wherein the carrier material (13) is divided into area regions, and within an area region only sensors (1) of one group are arranged,
area expansion of a sensor (1),
characterized in that the data measured by the sensor (1) is transmitted by the processing unit (5) to a central CPU (40), wherein this data is processed by the processing unit (5).

2. The measurement system (1000) according to claim 1, characterized in that the measuring system (1000) consists of two sensors (1), wherein the sensors
(1) are subdivided by the processing unit (5) into groups of at least one sensor (1) on the basis of at least one of the following criteria:
place of arrangement of the sensor(s) (1) on the support material (13), wherein the support material (13) is divided into surface zones, and within one surface zone only sensors (1) of one group are arranged,
surface area of a sensor (1).

3. The measurement system (1000) according to claim 1, characterised by at least two apparatuses (100) for measuring pressure and/or humidity, wherein each processing unit (5) transfers its data received from the sensors (1) to the central CPU (40).

4. The measurement system (1000) according to claim 1, characterized in that at least one apparatus (100) consists of two sensors (1).

5. The measurement system (1000) according to claim 1, characterized in that
at least one apparatus (100) comprises at least one temperature sensor (60), wherein the temperature sensor (60) measures an ambient temperature and/or a temperature of a sensor (1) and forwards it to the processing unit (5) of an apparatus (100) and/or to the central CPU (40).

6. The measurement system (1000) according to claim 1, in that the temperature sensor (60) measures a temperature of the processing unit (5) assigned thereto and forwards it to the processing unit (5) of an apparatus (100) and/or to the central CPU (40).

7. The measurement system (1000) according to claim 6, characterized in that
the central CPU (40) detects a degree of load (CPU load and/or memory consumption) of at least one processing unit (5) and, if a limit temperature of the processing unit (5)
and/or of at least one of the sensors (1) associated with said processing unit (5) is exceeded, the performance of said processing unit or sensor is at least partially restricted or completely shut down.

8. The measurement system (1000) according to claim 1, characterized by at least one processing network, wherein said network can be divided by means of at least one VLAN switch of the processing network into at least two network segments (VLANs) that are separated only logically from one another, and wherein each processing unit (5) and/or each of the sensors (1) can be controlled by each of the network segments, as a function of the control by the VLAN switch.

9. The measurement system (1000) according to claim 8, characterized in that a prioritization of the individual network segments is carried out by means of the VLAN switch with regard to the data exchange thereof.

10. A method for measuring pressure and/or humidity, initially comprising a first step by means of which a measuring system (1000) is provided, which comprises:
at least one sensor (1) for measuring pressure and/or humidity is provided, wherein the sensor (1) includes,
at least a first capacitor (20) comprising at least two electrodes (10, 11) that are arranged in a horizontal direction (H1) along and on an, in particular, flexible support material (13) relative to one another, wherein at least one dielectric layer (4) is arranged between the electrodes (10, 11),
the sensor (1) has at least one further capacitor (30) which is arranged in the transverse direction (Q1) above or below the first capacitor (20) and is arranged spaced apart from the first capacitor (20) by a further water-impermeable layer (14) on or below this further water-impermeable layer (4), so that a capacitor stack is formed, and further wherein
both capacitors (20, 30) are constructed in the same way, and further wherein the two sensors forming the capacitor stack perform the same tasks,
characterized in that
at least one at least partially liquid-permeable and/or liquid-absorbing moisture layer
(3) is arranged at least in some places on a side, facing away from the support material (13), of at least one electrode (10, 11) and/or of the dielectric layer (4), wherein the at least one electrode (10, 11) and/or the dielectric layer (4) are thus arranged between the support material (13) and the moisture layer (3) in a transverse direction (01), such that a capacitance is at least partially changed by
the liquid at least partially hitting the dielectric layer (4), wherein a processing unit
(5) measures and/or stores measurement values of the sensor (1), so as to create a capacitive moisture sensor, and further wherein,
the measuring system (1000) comprises at least two sensors (1), wherein by the processing unit (5) the sensors (1) are divided into groups of at least one sensor (1) based on at least one of the following criteria:
arrangement location of the sensor (1) or sensors (1) on the carrier material (13), wherein the carrier material (13) is divided into area regions, and within an area region only sensors (1) of one group are arranged,
area expansion of a sensor (1).

* * * * *